(12) United States Patent
Cusack et al.

(10) Patent No.: US 7,598,214 B2
(45) Date of Patent: Oct. 6, 2009

(54) DISINFECTING COMPOSITIONS CONTAINING A POLYMER COMPLEX OF AN ORGANIC ACID

(75) Inventors: Timothy Michael Cusack, Montvale, NJ (US); Karen Ann McCue, Montvale, NJ (US); Herbert W Ulmer, Bussum (NL)

(73) Assignee: Reckitt Benckiser Inc., Parsippany, NJ (US)

( * ) Notice: Subject to any disclaimer, the term of this patent is extended or adjusted under 35 U.S.C. 154(b) by 412 days.

(21) Appl. No.: 10/524,377

(22) PCT Filed: Aug. 14, 2003

(86) PCT No.: PCT/GB03/03549

§ 371 (c)(1),
(2), (4) Date: Mar. 18, 2005

(87) PCT Pub. No.: WO2004/016087

PCT Pub. Date: Feb. 26, 2004

(65) Prior Publication Data

US 2005/0159321 A1 Jul. 21, 2005

(30) Foreign Application Priority Data

Aug. 14, 2002 (GB) .................... 0218864.7

(51) Int. Cl.
*C11D 1/02* (2006.01)
*C11D 3/20* (2006.01)
*C11D 3/28* (2006.01)
*C11D 3/37* (2006.01)

(52) U.S. Cl. .................. 510/238; 510/191; 510/426; 510/476; 510/477; 510/488; 510/500; 510/505; 510/506

(58) Field of Classification Search ............ 510/191, 510/238, 426, 434, 476, 477, 488, 500, 505, 510/506
See application file for complete search history.

(56) References Cited

U.S. PATENT DOCUMENTS

| 3,532,771 | A | 10/1970 | Field et al. .............. 260/875 |
| 3,929,678 | A | 12/1975 | Laughlin et al. ............ 252/526 |
| 3,954,960 | A | 5/1976 | Valan ........................ 424/47 |
| 4,165,367 | A | 8/1979 | Chakrabarti ................ 424/47 |
| 4,223,009 | A | 9/1980 | Chakrabarti ................ 424/47 |
| 4,445,521 | A | 5/1984 | Grollier et al. ................ 132/7 |
| 4,521,404 | A | 6/1985 | Lorenz et al. ................ 424/71 |
| 4,767,788 | A | 8/1988 | Diana ........................ 514/574 |
| 4,828,912 | A | 5/1989 | Hossain et al. .............. 428/289 |
| 4,975,217 | A | 12/1990 | Brown-Skrobot et al. ... 252/107 |
| 5,734,006 | A | 3/1998 | Narayanan .................. 528/323 |
| 5,942,478 | A | 8/1999 | Lopes ........................ 510/130 |
| 6,034,133 | A | 3/2000 | Hendley et al. ............. 514/573 |
| 6,153,572 | A | 11/2000 | Stamm ........................ 510/193 |
| 6,225,429 | B1 | 5/2001 | Chuang et al. .............. 526/264 |
| 6,270,754 | B1 * | 8/2001 | Zhou et al. ................ 424/78.08 |
| 2002/0010099 | A1 | 1/2002 | Frisch et al. ................ 504/358 |
| 2002/0064542 | A1 | 5/2002 | Deckner et al. ............. 424/404 |

FOREIGN PATENT DOCUMENTS

| GB | 1331819 | | 9/1973 |
| WO | WO 96/17918 A1 | | 6/1996 |
| WO | WO 96/35645 A1 | | 11/1996 |
| WO | WO 00/00026 | | 1/2000 |
| WO | WO00/27271 | * | 5/2000 |
| WO | WO 02 28180 A | | 4/2002 |

OTHER PUBLICATIONS

International Search Report dated Oct. 14, 2003 for Application No. PCT/GB03/03549.
International Preliminary Examination Report dated Jun. 7, 2004 for Application No. PCT/GB03/03549.
Combined Search and Examination Report from The Patent Office in Great Britain dated Jan. 28, 2003 for Application No. GB 0218864.7.
Written Opinion dated Feb. 20, 2004 for Application No. PCT/GB03/03549.

* cited by examiner

*Primary Examiner*—Gregory R Del Cotto
(74) *Attorney, Agent, or Firm*—Norris McLaughlin & Marcus, PA

(57) ABSTRACT

The present invention provides compositions which not only effectively kill a broad spectrum of microorganisms present on surfaces on contact but continue to kill microorganisms for a period of time thereafter.

19 Claims, No Drawings

DISINFECTING COMPOSITIONS CONTAINING A POLYMER COMPLEX OF AN ORGANIC ACID

FIELD OF THE INVENTION

The present invention relates to improvements in disinfectant and disinfectant cleaning compositions. More particularly the present invention is related to the use of disinfectant and disinfectant cleaner compositions which not only effectively kills a broad spectrum of microorganisms (for example, bacteria, fungi, viruses, etc.) on contact but continues to kill microorganisms which are repeatedly deposited on the surfaces for hours after the surface is initially treated. The residual antimicrobial activity includes, but is not limited to, the common cold virus (*Rhinovirus*) and *Staphylococcus aureus*.

BACKGROUND OF THE INVENTION

Disinfectant and disinfectant cleaner compositions that effectively kill bacteria and viruses on a variety of surfaces are known in the art. These disinfectant compositions often contain well known classes of active ingredients such as alcohols, phenols, quaternary ammonium compounds, halogens, peroxides and acids. It is also known that certain actives kill a broad spectrum of organisms whereas others are limited in the types of organisms they kill. Also, certain organisms are sensitive to certain actives and physical conditions. The selection of actives and combination of actives for disinfecting is dependent primarily on the target organisms.

There are many common organisms in the environment, which are capable of causing infection. Among these are *Salmonella choleraesuis*, *E. coli* and *Staphylococcus aureus*, which are known to cause food poisoning, and *Rhinovirus*, which is the most significant cause of the common cold. *Rhinovirus* is a non-enveloped virus and is not readily inactivated by many common disinfecting compositions.

Most disinfectant compositions on the market today kill microorganisms on surfaces when applied and allowed to remain in contact for a specific time, typically 30 seconds to 10 minutes. However, after effectively killing those organisms present, the disinfectant does not typically persist on the surface. Normal stresses to the surface, like rinsing, repeated touching or wiping with a cloth, tend to physically remove any residual disinfectant ingredients from the surface. As a result, if the surface becomes recontaminated again the disinfectant must be re-applied to kill the newly deposited organisms.

It would be beneficial, particularly as a means of reducing the chance of infection, to have a disinfectant product that not only kills microorganisms on contact but also remains on the surface to continue to kill microorganisms that may subsequently recontaminate the surface. This invention relates to improvements in disinfectant and disinfectant cleaner compositions that are not only effective in killing microorganisms on contact but also provide a residual activity against microorganisms for a period of time thereafter under normal in-use conditions.

Others have investigated actives that separately eliminate the common cold virus and disinfectants that remain on the surface to provide residual activity. For example, U.S. Pat. Nos. 4,828,912 and 4,975,217, both assigned to Kimberly-Clark, disclose compositions comprising a certain concentration of acids such as citric and an anionic surfactant effective in killing *Rhinovirus* on skin. The composition can be incorporated into a variety of products for immediate virucidal activity but no long lasting activity is provided.

U.S. Pat. No. 4,767,788 to Diana discloses virucidal processes and compositions for inactivating *Rhinovirus* by contacting the virus with an effective amount of glutaric acid. Therein, it is disclosed that the virucidal effect only lasts up to 6 hours but does not include stresses of repeated wear or subsequent inoculations which would be expected under normal use conditions.

U.S. Pat. No. 6,034,133 to Hendley et al discloses a hand lotion composition contains organic acids, such as citric and malic acids, and a C1-6 alcohol and claims to kill *rhinovirus* and halt the hand to hand transmission of the virus. Therein, it is stated that frequent application of the composition will prevent hand to hand transmission of *Rhinovirus*, suggesting no residual activity rather than limited residual activity.

Published patent application WO 00/00026 to P&G discloses a premoistened wipe containing an organic acid and surfactant to give residual antimicrobial activity provided a specific amount of the organic acid and surfactant remain on the treated surface. Residual activity is claimed when treated surfaces are challenged only one time with a test organism. The efficacy under more practical conditions, such as repeated bacterial challenges or physical wear, over a 24 hour time period was not addressed. No additional agent which would facilitate keeping the active ingredient(s) on the surfaces is provided. There is no mention of residual virucidal activity.

In U.S. Pat. No. 6,270,754, Zhou et al. disclose an antibacterial cleaning composition, which shows germicidal activity for sustained periods of time. The composition includes a quaternary ammonium compound and an anionic polymer which form a polymer complex to provide sustained germicidal activity for the surface. The invention does not claim sustained virucidal activity. It is also known in the art quaternary ammonium compounds do not inactivate *Rhinovirus*.

Thus, there is a need for a composition that not only kills microorganisms, like the common cold virus, *Staphylococcus aureus*, or *Streptococcus*, on contact but also persists on surfaces to continue killing microorganisms which may be repeatedly deposited on said surfaces for an extended period of time. Compositions which can also provide a cleaning benefit are also desired. Methods of treating surfaces with these compositions are also important.

SUMMARY OF THE INVENTION

The present invention relates to a composition comprising at least one organic acid; optionally, at least one anionic surfactant; at least one polymer capable of forming a complex with at least one of the organic acids; optionally, at least one organic solvent; optionally, at least one propellant; water; and optionally, one or more further conventional constituents such as: pH buffering agents, perfumes, perfume carriers, colorants, hydrotropes, viscosity modifying agents, further germicides, fungicides, anti-oxidants, and anti-corrosion agents.

The present invention further relates to a composition comprising at least one organic acid, such as for example, citric acid, at least one anionic surfactant, such as for example, a secondary alkane sulfonate, and at least one polymer capable of forming a complex with at least one organic acid in a water or water and solvent base, preferably at a pH of <4.0. The choice of these ingredients is based on the antimicrobial activity and the performance desired. The organic acids and low pH are known to be effective in inactivating *Rhinovirus*, and acid:anionic active systems are employed for effective disinfecting against bacteria. Polymers are chosen based on compatibility and their ability to form complexes with at least one organic acid. Together, the organic acid:anionic surfactant polymer combination of the present invention provide enough active to be released to kill bacteria (gram negative and positive) and viruses (at a log reduction level of 1 log reduction or more) within a very short contact time (30 seconds) and maintain enough active in reservoir of the film to continue to be released over repeated microbial challenges over a period of time.

The present invention further relates to a composition comprising at least one organic acid, such as for example, citric acid, and at least one polymer capable of forming a complex with at least one organic acid in a water or water and solvent base, preferably at a pH of <4.0. The choice of these ingredients is based on the antimicrobial activity and the performance desired. Together, the organic acid:polymer combination of the present invention provide enough active to be effective against bacteria (gram negative) and viruses (at a log reduction level of 1 log reduction or more) within a very short contact time (30 seconds) and maintain enough active in reservoir of the film to continue to be released over repeated microbial challenges over a period of time.

Preferably, the amounts of each of the organic acid, anionic surfactant, when present, and polymer range from about 0.01 to about 10% wt, more preferably from about 0.1 to about 5% wt, and even more preferably from about 0.5 to about 2% wt. The ratio of organic acid:anionic surfactant (when present):polymer can range from about 1:1:1 to about 6:2:1, preferably from about 1:1:1 to about 4:2:1, and more preferably from about 1:1:1 to about 2:2:1.

The organic acid is selected from a compound having the formula:

R—COOH wherein R is hydrogen, lower alkyl; substituted lower alkyl; hydroxy lower alkyl; carboxy lower alkyl; carboxy, hydroxy lower alkyl; carboxy, halo lower alkyl; carboxy, dihydroxy lower alkyl; dicarboxy, hydroxy lower alkyl; carboxy lower alkenyl; dicarboxy lower alkenyl; phenyl; substituted phenyl, wherein substituted lower alkyl is substituted by one or more groups consisting of halogen, hydroxyl, amino, thiol, nitro, and cyano. Examples of acids include citric, malic, succinic, lactic, glycolic, fumaric, tartaric, and formic, etc.

The anionic surfactant, when present, is selected from the following classes: alcohol sulfates and sulfonates, alcohol phosphates and phosphonates, alkyl ester sulfates, alkyl diphenyl ether sulfonates, alkyl sulfates, alkyl ether sulfates, sulfate esters of an alkylphenoxy polyoxyethylene ethanol, alkyl monoglyceride sulfates, alkyl sulfonates, alkyl ether sulfates, alpha-olefin sulfonates, beta-alkoxy alkane sulfonates, alkyl ether sulfonates, ethoxylated alkyl sulfonates, alkylaryl sulfonates, alkylaryl sulfates, alkyl monoglyceride sulfonates, alkyl carboxylates, alkyl ether carboxylates, alkyl alkoxy carboxylates having 1 to 5 moles of ethylene oxide, alkylpolyglycolethersulfates (containing up to 10 moles of ethylene oxide), sulfosuccinates, octoxynol or nonoxynol phosphates, taurates, fatty taurides, fatty acid amide polyoxyethylene sulfates, acyl glycerol sulfonates, fatty oleyl glycerol sulfates, alkyl phenol ethylene oxide ether sulfates, paraffin sulfonates, alkyl phosphates, isethionates, N-acyl taurates, alkyl succinamates and sulfosuccinates, alkylpolysaccharide sulfates, alkylpolyglucoside sulfates, alkyl polyethoxy carboxylates, and sarcosinates or mixtures thereof. Alkyl sulfonates, alkyl sulfates, alkylaryl sulfates, and alkylaryl sulfonates (for example linear alkylbenzene sulfonates) are preferred.

The polymer is selected from the group
(1) polymer having the formula

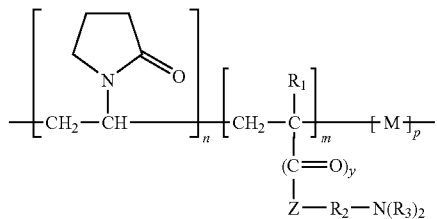

in which n represents from 20 to 99 and preferably from 40 to 90 mol %, m represents from 1 to 80 and preferably from 5 to 40 mol %; p represents 0 to 50 mol. (n+m+p=100); $R_1$ represents H or $CH_3$; y represents 0 or 1; Z is selected from O or NH; $R_2$ represents $C_xH_{2x}$, where x is 2 to 18; each of $R_3$ independently represents hydrogen or $C_1$ to $C_4$ alkyl; and M is a vinyl or vinylidene monomer copolymerisable with vinyl pyrrolidone other than the monomer identified in [ ]$_m$,
(2) vinylpyrrolidone/vinyl acetate copolymer,
(3) vinylpyrrolidone/vinyl caprolactam/ammonium derivative terpolymer, where the ammonium derivative monomer has 6 to 12 carbon atoms and is selected from dialkylamino alkyl methacrylamides, dialkylamino alkyl methacrylate, and dialkylamino alkyl acrylate,
(4) poly (vinyl pyrrolidone);
(5) vinyl pyrrolidone/vinyl caprolactam copolymer;
(6) vinyl pyrrolidonelacrylic acid (and its esters) or methacrylic acid (and its esters) copolymer; and
(7) a copolymer of Monomer A and Monomer B wherein Monomer A is of the formula $R^1$—CH=CH—$R^2$ and wherein Monomer B is of the formula $R^3$—C($R^1$)=C($R^2$)—$R^4$,
wherein $R^1$ and $R^2$ are independently selected from hydrogen; hydroxy; halogen;
carboxy; sulfo; phenyl; phenoxy; $C_{1-6}$ alkyl, $C_{1-6}$ alkoxy, $C_{1-6}$ aminoalkyl, $C_{1-6}$ haloalkyl wherein the halogen is selected from chlorine, bromine, iodine, and fluorine; $C_{1-6}$ alkylphenyl; amino and $C_{1-6}$ alkylamino, $R^3$ is an acidic group or a derivative thereof and $R^4$ is a group selected from any of the definitions given hereinbefore for $R^1$, $R^2$ or $R^3$, with the proviso that neither monomer A nor monomer B is an ester having a quaternary ammonium compound.

A copolymer comprising vinylpyrrolidone and dimethylaminoethylmethacrylate (for example, y is 1, x is 2, Z is O, p is 0 and each of $R_3$ are methyl) is an example of polymer (1). A copolymer comprising methyl vinyl ether and maleic anhydride (half ethyl ester) is an example of polymer (7).

Compositions of the present invention have residual activity on environmental surfaces when challenged with more than one inoculation of an organism or repeated wear challenges.

Methods of treating surfaces with the compositions of the present invention are also disclosed.

Another composition of interest is similar to those above except that no water is present and the materials of the composition are placed within a water soluble container, for example, a sachet made of poly(vinyl alcohol). The water soluble container can then be placed into a larger amount of water, where the water soluble container will dissolve, allowing the contents of the container to be dispersed within the amount of water thus forming a cleaning composition.

The present invention is also directed to a water soluble container containing a composition comprising at least one organic acid; at least one anionic surfactant; at least one polymer capable of forming a complex with at least one of the organic acids; optionally, at least one organic solvent; and optionally, one or more further conventional constituents such as: pH buffering agents, perfumes, perfume carriers, colorants, hydrotropes, viscosity modifying agents, further germicides, fungicides, anti-oxidants, and anti-corrosion agents.

Those skilled in the art will appreciate that the components that form the composition placed within the water soluble container will not contain water when those components are not available as 100 percent active materials.

DETAILED DESCRIPTION OF THE INVENTION

The present invention relates to a composition comprising at least one organic acid; optionally, at least one anionic surfactant; at least one polymer capable of forming a complex with at least one of the organic acids; optionally, at least one organic solvent; optionally, at least one propellant; water; and optionally, one or more further conventional constituents such as: pH buffering agents, perfumes, perfume carriers, colorants, hydrotropes, viscosity modifying agents, further germicides, fungicides, anti-oxidants, and anti-corrosion agents.

The present invention further relates to a composition comprising at least one organic acid, such as for example, citric acid, at least one anionic surfactant, such as for example, a secondary alkane sulfonate, and at least one polymer capable of forming a complex with at least one organic acid in a water or water and solvent base, preferably at a pH of <4.0. The choice of these ingredients is based on the antimicrobial activity and the performance desired. The organic acids and low pH are known to be effective in inactivating *Rhinovirus*, and acid:anionic active systems are employed for effective disinfecting against bacteria. Polymers are chosen based on compatibility and their ability to form complexes with at least one organic acid. Together, the organic acid:anionic surfactant:polymer combination of the present invention provide enough active to be released to kill bacteria (gram negative and positive) and viruses (at a log reduction level of 1 log reduction or more) within a very short contact time (30 seconds) and maintain enough active in reservoir of the film to continue to be released over repeated microbial challenges over a period of time.

The present invention further relates to a composition comprising at least one organic acid, such as for example, citric acid, and at least one polymer capable of forming a complex with at least one organic acid in a water or water and solvent base, preferably at a pH of <4.0. The choice of these ingredients is based on the antimicrobial activity and the performance desired. Together, the organic acid:polymer combination of the present invention provide enough active to be effective against bacteria (gram negative) and viruses (at a log reduction level of 1 log reduction or more) within a very short contact time (30 seconds) and maintain enough active in reservoir of the film to continue to be released over repeated microbial challenges over a period of time.

Preferably, the amounts of each of the organic acid, anionic surfactant, when present, and polymer range from about 0.01 to about 10% wt, more preferably from about 0.1 to about 5% wt, and even more preferably from about 0.5 to about 2% wt. The ratio of organic acid:anionic surfactant (when present): polymer can range from about 1:1:1 to about 6:2:1, preferably from about 1:1:1 to about 4:2:1, and more preferably from about 1:1:1 to about 2:2:1.

The organic acid is selected from a compound having the formula:

wherein R is lower alkyl; substituted lower alkyl; hydroxy lower alkyl (e.g. HOCH$_2$—); carboxy lower alkyl (e.g. HOOC—CH$_2$—CH$_2$—); carboxy, hydroxy lower alkyl (e.g., HOOCCH$_2$CHOH—); carboxy, halo lower alkyl (e.g. HOOCCH$_2$CHBr—); carboxy, dihydroxy lower alkyl (e.g. HOOC—CHOH—CHOH—); dicarboxy, hydroxy lower alkyl

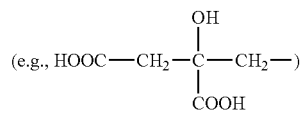

lower alkenyl, carboxy lower alkenyl (e.g. HOOCCH=CH—), dicarboxy lower alkenyl

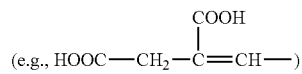

phenyl (C$_6$H$_5$—); substituted phenyl (e.g. hydroxy phenyl HO—C$_6$H$_4$—). Other acid examples include hydroxy lower alkyl e.g. lactic; carboxy, hydroxy lower alkyl, e.g. 2-methyl malic; carboxy, halo lower alkyl, e.g. 2-chloro-3-methyl succinic; carboxy, dihydroxy lower alkyl, e.g. 2-methyl tartaric; dicarboxy, hydroxy lower alkyl, e.g. 2-methyl citric acid; and carboxy lower alkenyl, e.g. fumaric. The above definitions are used in an illustrative but not a limiting sense. The term "lower" as used herein refers to an acid where "R" contains one to six carbon atoms. The term "substituted" indicates that one or more hydrogen atoms are substituted by halogen atoms (F, Cl, Br, I) hydroxyl groups, amino groups, thiol groups, nitro groups, cyano groups, etc. Examples of acids include citric, malic, succinic, lactic, glycolic, fumaric, tartaric, and formic, etc.

The anionic surfactant, when present, is selected from the following classes: alcohol sulfates and sulfonates, alcohol phosphates and phosphonates, alkyl ester sulfates, alkyl diphenyl ether sulfonates, alkyl sulfates, alkyl ether sulfates, sulfate esters of an alkylphenoxy polyoxyethylene ethanol, alkyl monoglyceride sulfates, alkyl sulfonates, alkyl ether sulfates, alpha-olefin sulfonates, beta-alkoxy alkane sulfonates, alkyl ether sulfonates, ethoxylated alkyl sulfonates, alkylaryl sulfonates, alkylaryl sulfates, alkyl monoglyceride sulfonates, alkyl carboxylates, alkyl ether carboxylates, alkyl alkoxy carboxylates having 1 to 5 moles of ethylene oxide, alkylpolyglycolethersulfates (containing up to 10 moles of ethylene oxide), sulfosuccinates, octoxynol or nonoxynol phosphates, taurates, fatty taurides, fatty acid amide polyoxyethylene sulfates, acyl glycerol sulfonates, fatty oleyl glycerol sulfates, alkyl phenol ethylene oxide ether sulfates, paraffin sulfonates, alkyl phosphates, isethionates, N-acyl taurates, alkyl succinamates and sulfosuccinates, alkylpolysaccharide sulfates, alkylpolyglucoside sulfates, alkyl polyethoxy carboxylates, and sarcosinates or mixtures thereof. Alkyl sulfonates, alkyl sulfates, alkylaryl sulfates, and alkylaryl sulfonates (for example linear alkylbenzene sulfonates) are preferred.

Further examples of anionic surfactants include water soluble salts or acids of the formula $(ROSO_3)_xM$ or $(RSO_3)_xM$ wherein R is preferably a $C_6$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a mono, di or trivalent cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like) and x is an integer, preferably 1 to 3, most preferably 1. Materials sold under the Hostapur and Biosoft trademarks are examples of such anionic surfactants.

Further examples of anionic surfactants include alkyl-diphenyl-ethersulphonates and alkyl-carboxylates. Other anionic surfactants can include salts (including, for example, sodium, potassium, ammonium, and substituted ammonium salts such as mono-, di-and triethanolamine salts) of soap, $C_6$-$C_{20}$ linear alkylbenzenesulfonates, $C_6$-$C_{22}$ primary or secondary alkanesulfonates, $C_6$-$C_{24}$ olefinsulfonates, sulfonated polycarboxylic acids prepared by sulfonabon of the pyrolyzed product of alkaline earth metal citrates, e.g., as described in British patent specification No. 1,082,179, $C_6$-$C_{24}$ alkylpolyglycolethersulfates (containing up to 10 moles of ethylene oxide); alkyl ester sulfates such as $C_{14\text{-}16}$ methyl ester sulfates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO^-M^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678 to Laughlin, et al. at column 23, line 58 through column 29, line 23. The above anionic surfactants are presented in an illustrative rather than a limiting sense.

The polymer is selected from the group
(1) polymer having the formula

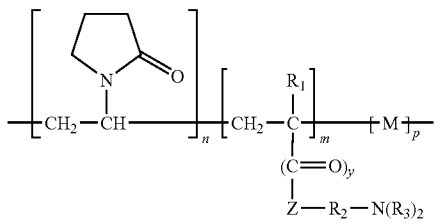

in which n represents from 20 to 99 and preferably from 40 to 90 mol %, m represents from 1 to 80 and preferably from 5 to 40 mol %; p represents 0 to 50 mol, (n+m+p=100); $R_1$ represents H or $CH_3$; y represents 0 or 1; Z is selected from O or NH; $R_2$ represents $C_xH_{2x}$ where x is 2 to 18; each of $R_3$ independently represents hydrogen or $C_1$ to $C_4$ alkyl; and M is a vinyl or vinylidene monomer copolymerisable with vinyl pyrrolidone other than the monomer identified in [ ]$_m$, (2) vinylpyrrolidonelvinyl acetate copolymer,
(3) vinylpyrrolidone/vinyl caprolactam/ammonium derivative terpolymer, where the ammonium derivative monomer has 6 to 12 carbon atoms and is selected from dialkylamino alkyl methacrylamides, dialkylamino alkyl methacrylate, and dialkylamino alkyl acrylate
(4) poly (vinyl pyrrolidone);
(5) vinyl pyrrolidone/vinyl caprolactam copolymer
(6) vinyl pyrrolidone/acrylic acid (and its esters) or methacrylic acid (and its esters) copolymer; and
(7) a copolymer of Monomer A and Monomer B wherein Monomer A is of the formula $R^1$—CH=CH—$R^2$ and wherein Monomer B is of the formula $R^3$—C($R^1$)=C($R^2$)—$R^4$,
wherein $R^1$ and $R^2$ are independently selected from hydrogen; hydroxy; halogen; carboxy; sulfo; phenyl; phenoxy; $C_{1\text{-}6}$ alkyl, $C_{1\text{-}6}$ alkoxy, $C_{1\text{-}6}$ aminoalkyl, $C_{1\text{-}6}$ haloalkyl wherein the halogen is selected from chlorine, bromine, iodine, and fluorine; $C_{1\text{-}6}$ alkylphenyl; amino and $C_{1\text{-}6}$ alkylamino, $R^3$ is an acidic group or a derivative thereof and $R^4$ is a group selected from any of the definitions given hereinbefore for $R^1$, $R^2$ or $R^3$, with the proviso that neither monomer A nor monomer B is an ester having a quaternary ammonium compound.

A first polymer (1) of interest is one having the formula

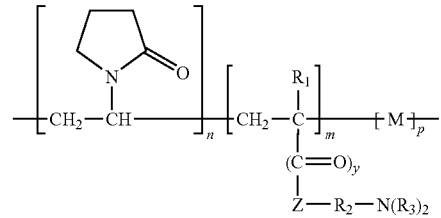

are more fully described in U.S. Pat. No. 4,445,521, U.S. Pat. No. 4,165,367, U.S. Pat. No. 4,223,009, U.S. Pat. No. 3,954,960, as well as GB1331819, the contents of which are hereby incorporated by reference, wherein the polymers for the present invention can be made according to the methods disclosed in the aforementioned documents but are used herein prior to any quaternization that the foregoing documents may disclose.

The monomer unit within [ ]$_m$ is, for example, a di-lower alkylamine alkyl acrylate or methacrylate or a vinyl ether derivative. Examples of these monomers include dimethylaminomethyl acrylate, dimethylaminomethyl methacrylate, diethylaminomethyl acrylate, diethylaminomethyl methacrylate, dimethylaminoethyl acrylate, dimethylaminoethyl methacrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminooctyl acrylate, dimethylaminooctyl methacrylate, diethylaminooctyl acrylate, diethylaminooctyl methacrylate, dimethylaminodecyl methacrylate, dimethylaminododecyl methacrylate, diethylaminolauryl acrylate, diethylaminolauryl methacrylate, dimethylaminostearyl acrylate, dimethylaminostearyl methacrylate, diethylaminostearyl acrylate, diethylaminostearyl methacrylate, di-t-butylaminoethyl methacrylate, di-t-butylaminoethyl acrylate, and dimethylamino vinyl ether.

Monomer M, which is optional (p is up to 50) can comprise any conventional vinyl monomer copolymerizable with N-vinyl pyrrolidone. Thus, for example, suitable conventional vinyl monomers include the alkyl vinyl ethers, e.g., methyl vinyl ether, ethyl vinyl ether, octyl vinyl ether, etc.; acrylic and methacrylic acid and esters thereof, e.g., methacrylate, methyl methacrylate, etc.; vinyl aromatic monomers, e.g., styrene, α-methyl styrene, etc; vinyl acetate; vinyl alcohol; vinylidene chloride; acrylonitrile and substituted derivatives thereof; methacrylonitrile and substituted derivatives thereof; acrylamide and methacrylamide and N-substituted derivatives thereof; vinyl chloride, crotonic acid and esters thereof; etc. Again, it is noted that such optional copolymerizable vinyl monomer can comprise any conventional vinyl monomer copolymerizable with N-vinyl pyrrolidone.

The film-forming polymers of the present invention are generally provided as a technical grade mixture which includes the polymer dispersed in an aqueous or aqueous/alcoholic carrier and are available in a variety of molecular weights from ISP Corp., Wayne, N.J.

An example of polymer (1) is a vinylpyrrolidone/dimethylaminoethylmethacrylate copolymer having the formula:

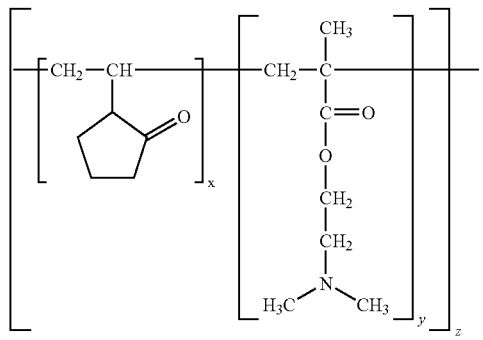

wherein x, y and z are at least 1 and have values selected such that the total molecular weight of the vinylpyrrolidone/dimethylamino ethylmethacrylate copolymer is at least 10,000 and can range up to an average molecular weight of about 1,200,000. Polymers of this type are available under tradename Copolymer 845, Co polymer 937, and Copolymer 958 from ISP.

Another example of polymer (1) is

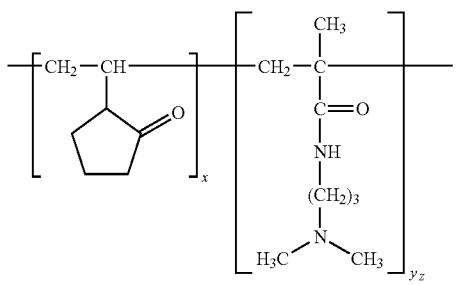

wherein x and y have values selected such that the total molecular weight is about 1,000,000 to about 5,000,000.

As provided for in GB1331819, page 3, lines 43 through 123, EXAMPLE 1 provides a process for making a copolymer useful in the present invention. Therein, a copolymer of N-vinyl pyrrolidone and dimethylaminoethyl methacrylate was produced utilizing polymerization apparatus comprising a 5 litre kettle equipped with mechanical stirrer, reflux condenser, thermometer, and gas inlet tube. Some 1,225 parts of ethanol as a solvent were charged into the kettle and 800 parts of N-vinyl pyrrolidone and 200 parts of dimethylaminoethyl methacrylate were added and agitation was started. To the system was added one part of azobisisobutyronitrile and the system was purged thoroughly with nitrogen. The temperature of the system was raised to gentle reflux at about 85° C. The polymerization reaction was promoted with further additions of catalyst (one part each) until the amount of residual monomer was below 0.6%. The system was thereafter cooled to 25° C. and the speed of the agitation was increased. For the polymer useful in the present invention, the quaternization step described in GB1331819 is not done.

Further in GB1331819, for EXAMPLE 2, Example 1 was repeated except that the dimethylaminoethyl methacrylate was replaced with substantially equivalent amounts of the following monomers:
  (a) dimethylaminomethyl acrylate
  (b) dimethylaminobutyl acrylate
  (c) diethylaminooctyl acrylate
  (d) diethylaminolauryl methacrylate
  (e) diethylaminostearyl methacrylate The polymerizations were conducted in the same manner as in Example 1, and the corresponding copolymers were produced except that for the present invention, the quaternization step is not done.

Further in GB1331819, for EXAMPLE 3, Example 1 was repeated except that the comonomers were employed in the following amounts:
  (f) 800 parts of N-vinyl pyrrolidone-100 parts dimethylaminoethyl methacrylate
  (g) 800 parts N-vinyl pyrrolidone-300 parts dimethylaminoethyl acrylate
  (h) 800 parts N-vinyl pyrrolidone-500 parts dimethylaminoethyl acrylate
  (i) 800 parts N-vinyl pyrrolidone-600 parts dimethylaminoethyl acrylate The polymerization was carried out as in Example 1. The corresponding copolymers were produced, the ratio of the monomers dictating the ratio of the monomeric functions in the copolymer product. For the polymer useful in the present invention, the quaternization step described in GB1331819 is not done.

Further in GB1331819, for EXAMPLE 4, Example 1 was repeated except that in addition to the dimethylaminoethyl methacrylate and N-vinyl pyrrolidone the following copolymerizable vinyl monomers were also utilized:
  (j) methyl vinyl ether-100 parts
  (k) octyl vinyl ether-280 parts
  (l) methacrylic acid-150 parts
  (m) methyl methacrylate-300 parts
  (n) styrene-200 parts
  (o) vinyl acetate-100 parts
  (p) vinylidene chloride-100 parts vinyl chloride-100 parts
  (q) methacrylonitrile-300 parts The terpolymers so produced by following the polymerization techniques of Example 1 all had molecular weights within the range of 15,000 to 1,000,000.

A second (2) polymer of interest include vinylpyrrolidone/vinylacetate copolymers which include those vinylpyrrolidone, vinylacetate copolymers, examples of which are presently commercially available. Such vinylpyrrolidone/vinylacetate copolymers are comprised of vinylpyrrolidone monomers which may be represented by the following structural formula:

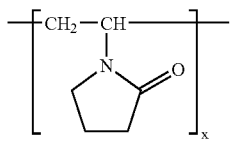

and vinylacetate monomers which may be represented by the following structural formula:

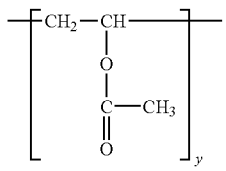

which are usually formed by a free-radical polymerization reaction to produce linear random vinylpyrrolidone/vinylacetate copolymers. The resultant vinylpyrrolidone/vinylacetate copolymers may comprise varying amounts of the individual vinylpyrrolidone monomers and vinylacetate monomers, with ratios of vinylpyrrolidone monomer to vinylacetate monomers from 30/70 to 70/30. The values of x and y in the structural formula should have values such that x+y=100 to 500, preferably x+y=150 to 300. The vinylpyrrolidone/vinylacetate copolymers will generally have a molecular weight in the range from about 10,000 to about 100,000, preferably from about 12,000 to about 60,000.

A third (3) polymer of interest includes vinylpyrrolidone/vinylcaprolactam/ammonium derivative terpolymers are comprised of vinylpyrrolidone monomers which may be represented by the following structural formula:

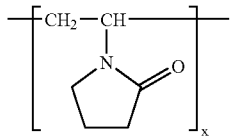

and vinylcaprolactam monomers which may be represented by the following structural formula:

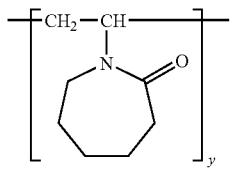

and ammonium derivative monomers which can be represented by one of the following structural formulae:

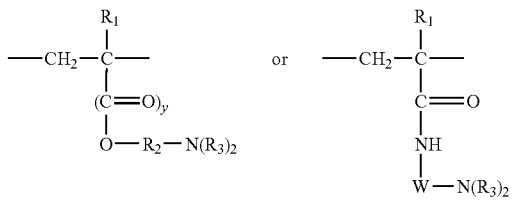

wherein $R_1$, $R_2$, $R_3$, y are described hereinabove and W is selected from

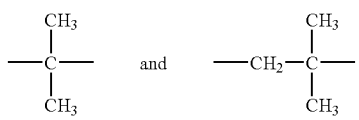

Exemplary vinylpyrrolidone/vinylcaprolactam/ammonium derivative terpolymer wherein the ammonium derivative monomer has 6 to 12 carbon atoms and is selected from dialkylamino alkyl methacrylamides, dialkylamino alkyl methacrylate, and dialkylamino alkyl acrylate which find use in the present inventive compositions are usually formed by a free-radical polymerization reaction to produce linear random vinylpyrrolidone/vinylcaprolactam/ammonium derivative terpolymers. The vinylpyrrolidone/vinylcaprolactam/ammonium derivative terpolymers useful in the present invention preferably comprise 17-32 weight % vinylpyrrolidone; 65-80 weight % vinylcaprolactam; 3-6 weight % ammonium derivative and 0-5 weight % stearyl methacrylate monomers. The polymers can be in the form of random, block or alternating structure having number average molecular weights ranging between about 20,000 and about 700,000; preferably between about 25,000 and about 500,000. Examples of the ammonium derivative monomer include, for example, dimethylamino propyl methacrylamide and dimethylamino ethyl methacrylate (DMAEMA). Examples of these terpolymers are described in U.S. Pat. No. 4,521,404 to GAF Corporation, the contents of which are hereby incorporated by reference.

A fourth (4) polymer of interest is polyvinylpyrrolidone. Examples of polymer (4) are well known in the art. The polyvinylpyrrolidone polymers generally exhibit a molecular weight of at least about 5,000, with a preferred molecular weight of from about 6,000-3,000,000. The polyvinylpyrrolidone is generally provided as a technical grade mixture of polyvinylpyrrolidone polymers within approximate molecular weight ranges. Such polyvinylpyrrolidone polymers are available in the PVP line materials (ex. ISP Corp.) which include PVP K 15 polyvinylpyrrolidone described as having molecular weight in the range of from 6,000-15,000; PVP-K 30 polyvinylpyrrolidone with a molecular weight in the range of 40,000-80,000; PVP-K 60 polyvinylpyrrolidone with a molecular weight in the range of 240,000-450,000; PVP-K 90 polyvinylpyrrolidone with a molecular weight in the range of 900,000-1,500,000; PVP-K 120 polyvinylpyrrolidone with a molecular weight in the range of 2,000,000-3,000,000. Other suppliers of polyvinylpyrrolidone include AllChem Industries Inc, Gainesville, Fla., Kraft Chemical Co., Melrose Park, Ill., Alfa Aesar, a Johnson Matthey Co., Ward Hill, Mass., and Monomer-Polymer & Dajac Labs Inc., Feasterville, Pa.

A fifth (5) polymer of interest is a copolymer of vinyl pyrrolidone/vinyl caprolactam. The ratio of vinyl pyrrolidone (VP) to vinyl caprolactam (VCL) can range from about 5 to about 95 VP:about 95 to about 5 VCL, preferably, from about 5 to 35 VP:about 95 to about 65 VCL. An example of polymer (5), vinyl pyrrolidone/vinyl caprolactam can be made according to a procedure, for example, from U.S. Pat. No. 6,225,429. Therein, Example 1 illustrates the preparation of vinyl pyrrolidone (VP)/vinyl caprolactam (VCL) (50/50) directly in water, after water according to a predetermined monomer feeding sequence, and without adding a protective colloid:

300.00 g of distilled water was charged into a 1-l resin kettle, fitted with a nitrogen inlet tube, an anchor agitator, a thermal watch/thermocouple probe and a heating mantle. After pH adjustment to 10 with 2 drops of concentrated ammonium hydroxide, nitrogen sparging was started and continued throughout the run. The kettle was then heated to 75° C. and maintained at 75° C. with an agitation speed at 250 rpm. A pre-charge mixture of 5.00 g of distilled vinyl pyrrolidone and 0.20 g of Lupersol 11M75 initiator (t-butyl peroxypivalate, 75% active), corresponding to 5% of total monomers, was pumped into the resin kettle over a period of 30 minutes. Thereafter, a mixture of 50.00 g of vinyl caprolactam (V-CAP/RC., ISP), 40.00 g of vinyl pyrrolidone and 0.60 g of Lupersol 11M75 initiator was pumped into the resin kettle over the next 60 minutes. The reaction mixture turned milky within 5 minutes upon charging of the monomer premix. Finally, a mixture of 5.00 g of vinyl pyrrolidone and 0.20 g of Lupersol 11M75 initiator was metered into the resin kettle over 30 minutes, followed by holding the reaction mixture at 75° C. for 60 minutes. 0.30 g of Lupersol 11M75 initiator was added and the reaction was held at 75° C. for 3 hours to react out residual monomers. The copolymer product was a milky-white dispersion in water at 75° C. Upon cooling, it gained in viscosity at 50-55° C. and became a substantially clear, viscous solution at room temperature. The solids content was adjusted to 25% in water. Gas chromatography (GC) analysis indicated that no residual VP or VCL monomer was present. The polymer had a cloud point of 55° C. (0.5% in water) and a relative viscosity of 2.027 (1% in water).

A sixth (6) polymer of interest is a copolymer of vinyl pyrrolidone/acrylic acid (and its esters) or methacrylic acid (and its esters). A typical run for preparing copolymers of vinyl pyrrolidone and acrylic acid (know as "Acrylidones") is described below.

A 1-liter, 4-necked reaction kettle was equipped with a mechanical stirrer, thermometer, dropping funnel and a nitrogen purge tube. The reactor was precharged with 75 g. of vinyl pyrrolidone in 500 g. of heptane. The solution then was heated to 65° C. during 20 minutes and held there for 30 min., while stirring under nitrogen gas. Then 260 microliter (0.3 g.) of t-butylperoxy pivalate initiator was added. Then 25 g. of acrylic acid was admitted during a period of 1 hour and the mixture was held for an hour. Then an additional 140 microliter (0.2 g.) of initiator was admitted into the reaction mixture and the solution was maintained at 65° C. with stirring for another 2 hours. Then another 100 microliter of initiator was added and the mixture held for 2 hours.

The reaction product then was cooled to room temperature during a period of about an hour. A fine white powder precipitate of copolymer product was obtained which was filtered, washed twice with heptane and dried overnight at 100° C. and then overnight again in a vacuum oven at 100° C. A 75:25 VP:AA copolymer (wt. ratio) was obtained in 97% yield. The product had a K-value of about 70 (1% copolymer in 0.1N NaOH and 0.2N LiNO$_3$ aqueous solution); the weight average molecular weight of the copolymer was about 20-80,000, as measured by light scattering in dimethylformamide solvent.

The procedure was followed using 99, 95, 50, 25 and 1 g. of vinyl pyrrolidone and 1, 5, 50, 75 and 99 g. of acrylic acid, to produce the corresponding 99:1, 95:5, 50:50, 25:75 and 1:99 wt. ratio VP:AA copolymers.

A seventh (7) polymer of interest is made from monomers A and B wherein monomer A is according to the formula:

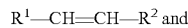

$R^1-CH=CH-R^2$ and monomer B is according to the formula:

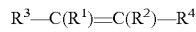

$R^3-C(R^1)=C(R^2)-R^4$ wherein $R^1$ and $R^2$ are independently selected from hydrogen; hydroxy; halogen; carboxy; sulfo; phenyl; phenoxy; $C_{1-6}$ alkyl, $C_{1-6}$ alkoxy, $C_{1-6}$ aminoalkyl, $C_{1-6}$ haloalkyl wherein the halogen is selected from chlorine, bromine, iodine, and fluorine, preferably chlorine; $C_{1-6}$ alkylphenyl; amino and $C_{1-6}$ alkylamino, $R^3$ is an acidic group or a derivative thereof and $R^4$ is a group selected from any of the definitions given hereinbefore for $R^1$, $R^2$ or $R^3$, with the proviso that neither monomer A nor monomer B is an ester having a quaternary ammonium compound.

According to an embodiment of the invention, monomer A is according to the formula:

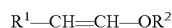

$R^1-CH=CH-OR^2$ wherein $R^1$ is as defined hereinbefore and $R^2$ is selected from phenyl, $C_{1-6}$ alkyl, $C_{1-6}$ aminoalkyl, $C_{1-6}$ haloalkyl, $C_{1-6}$ alkylphenyl, and $C_{1-6}$ alkylamino. More preferably, $R^1$ is hydrogen and $R^2$ is $C_{1-6}$ alkyl.

According to a further embodiment, monomer B is a dibasic acid according to the formula:

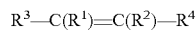

$R^3-C(R^1)=C(R^2)-R^4$ in which $R^3$ and $R^4$ are both carboxyl and $R^1$ and $R^2$ are as defined hereinbefore, and according to an embodiment of the invention both $R^1$ and $R^2$ are hydrogen.

It is preferred that when the copolymer of the invention is comprised of more than two monomers, monomers A and B form at least 90% in moles of the total copolymer. It is further preferred that the molar ratio of monomers A and B is from 60:40 to 40:60, it being most preferred that the copolymer comprises a substantially equal molar content of monomers A and B.

The copolymer of the invention may further comprise monomers C, which may form up to 10% in moles of the total copolymer and individually, may form up to 5% in moles of the total monomer. The additional monomers may be any ethylenically unsaturated monomer provided that they are polymerisable with monomers A and B. The additional monomer may occupy any position in the polymer chain, but preferably the additional monomers are homogeneously dispersed.

According to a further embodiment of the invention, $R^3$ in monomer B is a sulfo or carboxy group or a derivative thereof and $R^4$ is an acidic group or a derivative thereof, preferably also a sulfo or carboxy group or a derivative thereof. When two contiguous carboxy groups are present in the copolymer of the invention, the cyclic anhydride derivative may be also usefully employed.

The acidic groups of monomers A and B can be defined as meaning that all the acidic groups of the monomers may be present either as free acidic groups or as corresponding anhydrides or alternatively, as derivatives or as derivatives that can be formed from said free acid groups or corresponding anhydrides, for example, esters, salts, amino-ammonium salts, amides, imides, complexes with inorganic and organic compounds etc, by reaction under suitable conditions conventionally used.

Specific examples of monomer A include, but are not limited to: alkyl vinyl ethers selected from vinyl methyl ether, vinyl ethyl ether, vinyl propyl ether, vinyl isopropyl ether, vinyl n-butyl ether, vinyl isobutyl ether, vinyl n-amyl ether, vinyl n-hexyl ether; and alkoxy alkyl vinyl ethers selected from methoxyethyl vinyl ether, ethoxyethyl vinyl ether, propoxyethyl vinyl ether, butoxyethyl vinylether, methoxyethoxyethyl vinyl ether, ethoxyethoxyethyl vinyl ether, butoxyethoxyethyl vinyl ether.

The most preferred copolymer according to the invention is one in which monomer A is methyl vinyl ether and monomer B is maleic acid or a derivative thereof, more preferably, monomer B is a cyclic anhydride of maleic acid (maleic anhydride).

Copolymers of methyl vinyl ether and maleic acid/maleic anhydride are commercially available and sold under the tradename GANTREZ, available from International Specialty Products (ISP), New Jersey, U.S.A. For example these copolymers include, Gantrez AN-119 copolymer (molecular weight of approximately 20,000), Gantrez AN-139 copolymer (molecular weight of approximately 41,000), Gantrez AN-149 copolymer (molecular weight of approximately 50,000), Gantrez AN-169 copolymer (molecular weight of approximately 67,000), Gantrez AN-179 copolymer (molecular weight of approximately 80,000), Gantrez MS-955 (mixed calcium and sodium salt blend of the methyl vinyl etherimaleic acid copolymer, in which the proportion of Ca:Na is about 5-6:1 and the molecular weight is about 65,000-70,000), Gantrez S-97 (copolymer has intact acid groups), Gantrez ES-353 (monoisopropyl ester derivative of the copolymer) and Gantrez ES-435 and ES-425 (monobutyl ester derivatives of the copolymer).

Copolymers of interest for polymer (7) useful in the present invention, have the following formulae:

methyl vinyl ether and maleic anhydride

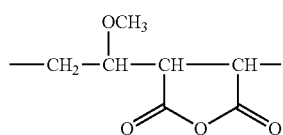

or methyl vinyl ether and maleic acid

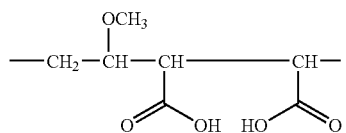

or derivatives of such compounds. The derivatives of these copolymers are selected from free acidic forms of said copolymers; esterified derivatives of said copolymers and salts thereof; amide derivatives or imide derivatives of the copolymers or salts thereof, or mixed amide/imide derivatives of said copolymers or salts thereof; complexes of said copolymers and iodine formed, for example, when iodine is added to an aqueous solution of the copolymer; complexes of said copolymers and polyvinyl pyrrolidone; and derivatives obtained from the reaction of said copolymers with polyhydroxy compounds and polyamines, in particular, derivatives obtained from partial or complete neutralization of the acidic groups with glycerin, glycols, polyglycols, polyvinyl alcohol, pentaerythritol, sorbitol, diols and polydiols and the like.

The free acid derivative of the copolymer of the invention, may be formed when the copolymer is dissolved in water to cause the anhydride linkage to be cleaved to form the highly polar, polymeric free acid. The corresponding partial ester is formed if the copolymer is dissolved in alcohol, for example, mono-hydroxy acyclic, saturated cyclic, aromatic, and terpenic alcohols or phenols. Both these derivatives of the preferred methyl vinyl ether/maleic anhydride copolymer of the invention are commercially available from ISP, New Jersey under the tradenames Gantrez S and Gantrez ES series (registered trademarks), respectively, and have the formulae:

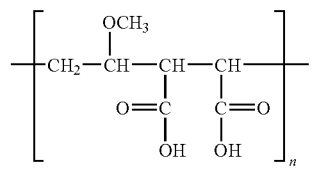

free acid derivative of the poly(methyl vinyl ether/maleic anhydride) copolymner obtained by dissolving Gantrez AN in water, which reacts with the anhydride group to form the acid and

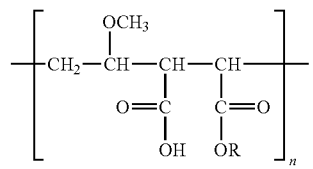

mono-ester derivative of the poly(methyl vinyl ether/maleic anhydride) copolymer, wherein R is ethyl, isopropyl or butyl.

In each case, n is determined by the required molecular weight of the polymer.

Esterification can also occur when anhydride copolymers of the invention are added directly to a nonionic surfactant or to an aqueous solution thereof.

The copolymers of polymer (7) are commercially available and produced by conventional polymerization methods, which will depend on the properties of the specific monomers used. Hence, any known polymerization method suitable for polymerization of ethylenically unsaturated monomers may be used, for example, bulk polymerization, solution polymerization, emulsion polymerization, suspension polymerization etc. Copolymers of alkyl vinyl ethers, for example, methyl vinyl ether and maleic anhydride, can be prepared in accordance with the polymerization method described in U.S. Pat. No. 3,532,771.

Organic solvents are an optional component to the present invention. Suitable antimicrobial activity can be achieved without the use of organic solvents. When present, the organic solvents that can be used in the present invention are generally those solvents which can solublize the components of the present invention without affecting the activity of those components. These types of solvents include alcohols, glycols, glycol ethers, ethers, and the like. Preferred solvents include those solvents, preferably alcohols, which are known to have antimicrobial activity such as methanol, ethanol, n-propanol, isopropanol, n-butanol, benzyl alcohol, and mixtures thereof. The amount of solvent, when present, can range from about 1 to about 90% wt.

Water is added to order to provide to 100% by weight of the compositions of the invention. The water may be tap water, but is preferably distilled and is most preferably deionized water. If the water is tap water, it is preferably substantially free of any undesirable impurities such as organics or inorganics, especially mineral salts which are present in hard water which may thus undesirably interfere with the operation of the constituents present in the aqueous compositions according to the invention.

As discussed previously, the inventive compositions may comprise one or more conventional optional additives. By way of non-limiting example, these include: pH adjusting agents and pH buffers including organic and inorganic salts; non-aqueous solvents, perfumes, perfume carriers, optical brighteners, coloring agents such as dyes and pigments, opacifying agents, hydrotropes, antifoaming agents, viscosity modifying agents such as thickeners, enzymes, anti-spotting agents, anti-oxidants, anti-corrosion agents as well as others not specifically elucidated here. These ingredients may be present in any combinations and in any suitable amount that is sufficient for imparting the desired properties to the compositions. These one or more conventional additives, when present, should be present in minor amounts, preferably in total comprise less than about 5% by weight (on an active weight basis) of the compositions, and desirably less than about 3% wt.

Compositions of the present invention have residual activity on surfaces when challenged repeatedly (i.e. more than one inoculation) with microorganisms.

In addition to the organic acid, anionic surfactant, polymer, optional organic solvent, balance of the composition will be water, and optionally, surfactants, fragrances, salts and colors, known in the art to enhance performance and aesthetic appeal. The compositions may be either ready to use or in concentrated form. The compositions can be incorporated into wipes, hard surface disinfectants and cleaners, sanitizers, dishwashing (including automatic dish), products, including rinse aids, laundry and fabric treatment products, health and personal care products such as antiseptics, hand soaps and lotions to kill or prevent the spread of microorganisms.

Several examples of organic acid, anionic surfactant, and polymer were formulated in water and water:ethanol solutions as set forth in Table 1 below.

A general procedure for preparing the organic acid-anionic surfactant-polymer composition is shown below. In those compositions where an organic solvent is not used, that step, or part of the step, of the procedure can be eliminated.

Step 1) All organic solvent and ¾ the water is added to an appropriately sized vessel and stirred Step 2) To the stirred organic solvent/water solution is added the polymer and anionic surfactant Step 3) The solution of Step 2) is stirred until the polymer is homogeneously dissolved Step 4) The organic acid is dissolved in the remaining ¼ water Step 5) The organic acid/water solution from Step 4) is gradually added to the solution of Step 3) while being stirred to give the polymer/active solution An actual formulation (1000 grams) using the above general procedure was used to make the following composition:

591.65 grams ethanol and 263.74 grams water were added to a suitably sized vessel and stirred. To the stirred ethanol/water mixture was added 16.70 grams Copolymer 958 (50% solids in ethanol) and 25.00 grams Biosoft D-40 (40% active in water). The ethanol/water/polymer the mixture was allowed to stir until the polymer was homogeneously dissolved throughout the solution. 15.00 grams citric acid was dissolved in 87.91 grams water. The citric acid/water solution was gradually added to the mixing vessel containing the ethanol/water/polymer solution with stirring. The resultant solution was crystal clear.

The Examples Ex. 2 to Ex. 15 in Table 1 were made according to the above procedure. The amounts shown in Table 1 are in active amounts, not as received from suppliers.

TABLE 1

| Components | Ex. 1 | Ex. 2 | Ex. 3 | Ex. 4 | Ex. 5 | Ex. 6 | Ex. 7 | Ex. 8 |
|---|---|---|---|---|---|---|---|---|
| Copolymer 958[1] | | 2.0 | 2.0 | 1.0 | 0.75 | 1.0 | 1.5 | |
| Copolymer 937[2] | | | | | | | | 0.5 |
| Citric Acid | 1.0 | 1.0 | 1.0 | 1.0 | 1.0 | 2.0 | 2.0 | |
| Hostapur SAS[3] | 0.5 | 0.5 | 0.5 | 0.5 | 0.5 | 2.0 | 1.0 | 0.75 |
| Ethanol | | | 80.0 | 80.0 | 80.0 | 80.0 | 80.0 | 60 |
| Water | q.s. | q.s. | q.s. | q.s. | q.s. | q.s. | q.s. | q.s. |

| Components | Ex. 9 | Ex. 10 | Ex. 11 | Ex. 12 | Ex. 13 | Ex. 14 | Ex. 15 |
|---|---|---|---|---|---|---|---|
| Copolymer 958[1] | 1 | 1 | 1 | 0.5 | 1 | 0.83 | 0.83 |
| Citric Acid | 2 | 2 | 2 | 2 | 2 | 1.5 | 1.5 |
| Hostapur SAS | 2 | 2 | | | | | |
| Biosoft D40[4] | | | 2 | 1 | | 1 | 0.5 |
| Alpha Step MC-48[5] | | | | | 2 | | 0.5 |
| Ethanol | 80 | 60 | 60 | 60 | 60 | 60 | 60 |
| Water | q.s. | q.s. | q.s. | q.s. | q.s. | q.s. | q.s. |

[1] a copolymer of vinylpyrrolidone with dimethylaminoethylmethacrylate (ISP)
[2] a copolymer vinylpyrrolidone and t-butylaminoethyl methacrylate (ISP)
[3] sodium $C_{14}$-$C_{17}$ secondary alkane sulfonate (Clariant)
[4] linear alkylbenzene sulfonate, sodium (Stepan)
[5] sodium alphasulfo methyl $C_{12-18}$ ester and disodium alphasulfo $C_{12-18}$ fatty acid salt (Stepan)

The compositions in Table 1 were evaluated for log reduction activity and residual performance against *Enterobacter aerogenes* after 2, 10, 20, 25, 35, and 50 inoculations (INCS)

following the "Interim Guidance for Residual Self-Sanitizing of Dried Chemical Residues on Hard Inanimate Surfaces" recommended by the United States Environmental Protection Agency (EPA). Compositions were applied to a hard non-porous glazed tile and allowed to air dry. Inoculations to achieve at least a $10^4$ concentration of bacteria and virus was subsequently applied to the treated surface. This regimen of inoculations was repeated for 1-50 times. After each selected inoculation, the organisms remained in contact with the treated surface for 30 seconds for action to take place. After the 30 second contact time, the surface was sampled and enumerated for number of surviving organisms. The results are shown in Table 2 below.

TABLE 2

Residual Activity vs. *Enterobacter aerogenes* (Log Reduction - 30 second contact)

|        | 2 INCS | 10 INCS | 20 INCS | 25 INCS | 35 INCS | 50 INCS |
|--------|--------|---------|---------|---------|---------|---------|
| Ex. 1  | 0.98   | NT*     | NT      | NT      | NT      | NT      |
| Ex. 2  | 2.89   | NT      | NT      | NT      | NT      | NT      |
| Ex. 3  | 3.63   | 0       | NT      | NT      | NT      | 1.52    |
| Ex. 4  | 3.13   | 2.91    | NT      | NT      | NT      | NT      |
| Ex. 5  | NT     | 4.76    | NT      | 2.21    | NT      | NT      |
| Ex. 6  | NT     | 4.76    | NT      | 5.29    | 5.0     | 5.0     |
| Ex. 7  | NT     | NT      | NT      | NT      | 5.0     | 3.32    |
| Ex. 8  | NT     | 3.11    | 2.81    | NT      | NT      | NT      |
| Ex. 9  | NT     | 4.61    | 2.81    | NT      | NT      | NT      |
| Ex. 10 | NT     | 3.72    | 3.14    | NT      | NT      | NT      |
| Ex. 11 | NT     | 4.25    | NT      | NT      | NT      | 2.73    |
| Ex. 12 | NT     | 4.25    | NT      | NT      | NT      | 3.7     |
| Ex. 13 | NT     | NT      | NT      | NT      | NT      | 4.16    |
| Ex. 14 | NT     | NT      | NT      | NT      | NT      | 5.11    |
| Ex. 15 | NT     | NT      | NT      | NT      | NT      | 3.25    |

*not tested

Composition Ex. 1 without polymer does not provide at least a 1 log reduction in activity after 2 innoculations for residual performance. The presence of the polymer in either water (Ex. 2) or ethanol solvent (Ex. 3) base enables log reduction activity of the active components after 2 innoculations, demonstrating residual performance. The results further show that varied concentrations of polymer and actives (acid and anionic) will result in varied log reduction levels of residual activity. Formulation Ex. 3, with a higher content of copolymer 958 than actives shows high (>3 log reduction) residual performance after 2 repeated inoculations but loses some activity after 10 repeated inoculations, whereas formulation Ex. 5 with a lower content of copolymer 958 than actives demonstrates high residual activity (>3 log reduction) even after 10 inoculations with 4.7 log reduction. Formulations Ex. 6 and Ex. 7 further shows that certain levels of polymer and active levels can extend the residual sanitizing ($\geqq 3$ log reduction) performance to as far as at least 50 repeated inoculations.

Table 3 shows log reduction activity against *S. aureus* and *Rhinovirus* after 50 repeated inoculations (30 second contact time). Ex. 6 and Ex. 7 demonstrate extended residual sanitizing (>3 log reduction) activity against both bacteria and viruses including *Enterobacter aerogenes* (Table 2), *Staphylococcus aureus* and *Rhinovirus* (Table 3) in a very short contact time for at least 50 repeated inoculations. Formulation Ex. 14 also demonstrates extended residual sanitizing activity against *Enterobacter aerogenes* (Table 2) and *Staphylococcus aureus* (Table 3) in a very short contact time for at least 50 repeated inoculations.

TABLE 3

Residual Activity (Log Reduction - 30 seconds)

| Formulation | *Staphylococcus aureus* - 50 inoculations | Rhinovirus - 50 inoculations |
|-------------|-------------------------------------------|------------------------------|
| Ex. 6       | 4.56                                      | >3.0                         |
| Ex. 7       | 4.06                                      | >3.0                         |
| Ex. 14      | 4.81                                      | NT                           |

Table 4 shows residual antimicrobial performance after repeated wear (rinses with water) of the surface and inoculation with *Salmonella choleraesuis*, *Staphylococcus aureus* and *Rhinovirus*. Results show that compositions of polymer and organic acid demonstrate residual log reduction activity against *Salmonella choleraesuis* and *Rhinovirus* but not *Staphylococcus aureus* after 4 repeated wear (rinses with water) challenges.

TABLE 4

| Composition (amounts are on "active basis"; 75% ethanol; balance is water) | Log reduction v. *Salmonella choleraesuis* | | Log reduction v. *Staphylococcus aureus* | |
|---|---|---|---|---|
| | 1 rinse | 4 rinses | 1 rinse | 4 rinses |
| Ex. 16 (3% Polymer (2A[1]), 1% Acid[5]) | 4.81 | 4.28 | 0.31 | NT |
| Ex. 17 (3% Polymer 2B[2]), 1% Acid) | 5.1 | 4.22 | 0 | NT |
| Ex. 18 (3% Polymer (7[3]), 1% Acid) | 5.4 | 3.8 | 0.07 | NT |
| Ex. 19 (3% Polymer (6[4]), 1% Acid) | 6.4 | 6.26 | 0.73 | NT |
| Ex. 20 (3% Polymer (2A)) | 0 | NT | 0.26 | NT |
| Ex. 21 (3% Polymer (2B)) | 0 | NT | 0.25 | NT |
| Ex. 22 (3% Polymer (7)) | 0 | NT | 0.13 | NT |
| Ex. 23 (3% Polymer (6)) | 0.71 | NT | 0 | NT |
| Control-log recovery | 6.4 | | 6.28 | |

| Composition (amounts are on "active basis"; 75% ethanol; balance is water) | Log reduction v. *Rhinovirus* | | Log reduction v. *Rhinovirus* | |
|---|---|---|---|---|
| | 1 rinse | 4 rinses | 1 rinse | 4 rinses |
| Ex. 16 (3% Polymer (2A), 1% Acid) | 2.34 | 2.17 | | |
| Ex. 17 (3% Polymer (2B), 1% Acid) | >4.17 | >4.17 | | |
| Ex. 18 (3% Polymer (7), 1% Acid) | >4.17 | >4.17 | | |

TABLE 4-continued

| | | | | |
|---|---|---|---|---|
| Ex. 19 (3% Polymer (6), 1% Acid) | >4.17 | >4.17 | | |
| Ex. 20 (3% Polymer (2A)) | 1 | NT | | |
| Ex. 21 (3% Polymer (2B)) | 0 | NT | | |
| Ex. 22 (3% Polymer (7)) | 2 | NT | | |
| Ex. 23 (3% Polymer (6)) | >4.17 | NT | >5.17 | >5.17 |
| Control-log recovery | 5.67 | | 6.67 | 6.67 |

[1]Polymer (2A) = vinyl pyrrolidone/vinyl acetate (30/70; supplied as 50% active in ethanol)
[2]Polymer (2B) = vinyl pyrrolidone/vinyl acetate (50/50; supplied as 50% active in isopropanol)
[3]Polymer (7) = methyl vinyl ether/maleic acid ethyl half ester (supplied as 50% active in ethanol)
[4]Polymer (6) = vinyl pyrrolidone/acrylic acid (50/50; supplied as 100% active)
[5]Acid = citric acid The compositions according to the invention are desirably provided as a ready to use product which may be directly applied to a hard surface. Hard surfaces which are to be particularly denoted are lavatory fixtures, lavatory appliances (toilets, bidets, shower stalls, bathtubs and bathing appliances), wall and flooring surfaces especially those which include refractory materials and the like. Further hard surfaces which are particularly denoted are those associated with dishwashers, kitchen environments and other environments associated with food preparation. Hard surfaces which are those associated with hospital environments, medical laboratories and medical treatment environments. Such hard surfaces described above are to be understood as being recited by way of illustration and not be way of limitation. The compositions of the present invention can also be applied to skin or soft (e.g., fabric or textile) surfaces.

The compositions provided according to the invention can be desirably provided as a ready to use product in a manually operated spray dispensing container, or may be supplied in aerosolized product wherein it is discharged from a pressurized aerosol container. Propellants which may be used are well known and conventional in the art and include, for example, a hydrocarbon, of from 1 to 10 carbon atoms, such as n-propane, n-butane, isobutane, n-pentane, isopentane, and mixtures thereof; dimethyl ether and blends thereof as well as individual or mixtures of chloro-, chlorofluoro- and/or fluorohydrocarbons- and/or hydrochlorofluorocarbons (HCFCs). Useful commercially available compositions include A-70 (Aerosol compositions with a vapor pressure of 70 psig available from companies such as Diversified and Aeropress) and Dymel 152a (1,1-difluoroethane from DuPont). Compressed gases such as carbon dioxide, compressed air, nitrogen, and possibly dense or supercritical fluids may also be used. In such an application, the composition is dispensed by activating the release nozzle of said aerosol type container onto the area in need of treatment, and in accordance with a manner as above-described the area is treated (e.g., cleaned and/or sanitized and/or disinfected). If a propellant is used, it will generally be in an amount of from about 1% to about 50% of the aerosol formulation with preferred amounts being from about 2% to about 25%, more preferably from about 5% to about 15%. Generally speaking, the amount of a particular propellant employed should provide an internal pressure of from about 20 to about 150 psig at 70° F.

The compositions according to the invention can also be suited for use in a consumer "spray and wipe" application as a cleaning and/or sanitizing and/or disinfecting composition. In such an application, the consumer generally applies an effective amount of the composition using the pump and within a few moments thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposits after which it may then be wiped off, rinsed off, or otherwise removed. For particularly heavy deposits of such undesired stains, multiple applications may also be used. Where thorough disinfection is a primary consideration, it may be desired to apply the inventive compositions to the surface being treated and to permit the composition to remain on the surface for several minutes (2-10 min.). If so desired, after the composition has remained on the surface for a period of time, it could be rinsed or wiped from the surface.

Whereas the compositions of the present invention are intended to be used in the types of liquid forms described, nothing in this specification shall be understood as to limit the use of the composition according to the invention with a further amount of water to form a cleaning solution therefrom. In such a proposed diluted cleaning solution, the greater the proportion of water added to form said cleaning dilution will, the greater may be the reduction of the rate and/or efficacy of the thus formed cleaning solution. Accordingly, longer residence times upon the stain to effect their loosening and/or the usage of greater amounts may be necessitated. Conversely, nothing in the specification shall be also understood to limit the forming of a "super-concentrated" cleaning composition based upon the composition described above. Such a super-concentrated ingredient composition is essentially the same as the cleaning compositions described above except in that they include a lesser amount of water.

The composition of the present invention, whether as described herein or in a concentrate or super concentrate form, can also be applied to a hard surface by using a wet wipe. The wipe can be of a woven or non-woven nature. Fabric substrates can include nonwoven or woven pouches, sponges, in the form of abrasive or non-abrasive cleaning pads. Such fabrics are known commercially in this field and are often referred to as wipes. Such substrates can be resin bonded, hydroentangled, thermally bonded, meltblown, needlepunched, or any combination of the former.

The nonwoven fabrics may be a combination of wood pulp fibers and textile length synthetic fibers formed by well known dry-form or wet-lay processes. Synthetic fibers such as rayon, nylon, orion and polyester as well as blends thereof can be employed. The wood pulp fibers should comprise about 30 to about 60 percent by weight of the nonwoven fabric, preferably about 55 to about 60 percent by weight, the remainder being synthetic fibers. The wood pulp fibers provide for absorbency, abrasion and soil retention whereas the synthetic fibers provide for substrate strength and resiliency.

The substrate of the wipe may also be a film forming material such as a water soluble polymer. Such self-supporting film substrates may be sandwiched between layers of fabric substrates and heat sealed to form a useful substrate. The free standing films can be extruded utilizing standard equipment to devolatilize the blend. Casting technology can be used to form and dry films or a liquid blend can be saturated into a carrier and then dried in a variety of known methods.

The compositions of the present invention are absorbed onto the wipe to form a saturated wipe. The wipe can then be sealed individually in a pouch which can then be opened when needed or a multitude of wipes can be placed in a container for use on an as needed basis. The container, when closed, sufficiently sealed to prevent evaporation of any components from the compositions. In use, a wipe is removed from the container and then wiped across an area in need of treatment. The mechanical (and composition) action can act to remove stains and remnants of the compositions are left behind to provide a residual benefit.

Antibacterial personal care compositions, such as soaps, lotions and antiseptics are typically are used to cleanse or treat the skin and to destroy microorganisms present on the skin, especially the hands, arms, and face of the user. These types of compositions typically contain an active antibacterial agent, a surfactant, and various other ingredients, for example, dyes, fragrances, pH adjusters, thickeners, skin conditioners, and the like, in an aqueous carrier. Herein, the inventive composition provides the active antibacterial agent for these personal care items.

Laundry or fabric treatment compositions and dishwashing compositions, including rinse aids, are well know to those of ordinary skill in the art. While the compositions may be different because of sudsing or foaming properties (for example, a high sudsing or foaming surfactant may be preferable for a laundry application but not for an automatic dishwashing application), the inventive composition of the present application can be used in place of the more common antimicrobials used in laundry or dishwashing applications. Quaternary ammonium compounds can be used to impart antimicrobial activity to laundry or dishwashing compositions. In using such materials, this limits the types of materials to be used in the those compositions because of interactions between quaternary ammonium compounds and anionic surfactants, for example. Using the present inventive composition in place of the quaternary ammonium compounds would provide for more flexibility in developing laundry or dishwashing compositions since there would no longer be the issue of interaction between quaternary ammonium compounds and anionic surfactants.

This invention solves the need for a disinfectant product that not only kills microorganisms like the common cold virus on contact but will also remain on the surface so it can continue to be effective in killing microorganisms that contaminate the surfaces for an extended period of time.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A hard surface treatment composition providing a residual antimicrobial benefit to hard surfaces comprising:
    (a) at least one organic acid;
    (b) optionally, at least one anionic surfactant;
    (c) at least one polymer capable of forming a complex with (a) at least one of organic acid wherein the at least one polymer is selected from the group consisting of a copolymer of vinyl pyrrolidone/acrylic acid and its esters; and a copolymer of vinyl pyrrolidone/methacrylic acid and its esters copolymer; and
    (d) from 60% to 90% by weight of at least one organic solvent;
    (e) optionally, at least one propellant;
    (f) water; and
    optionally, one or more further conventional constituents selected from the group consisting of: pH buffering agents, perfumes, perfume carriers, colorants, hydrotropes, viscosity modifying agents, further germicides, fungicides, anti-oxidants, and anti-corrosion agents.

2. The composition according to claim 1 wherein the at least one organic acid is selected from a compound having the formula:

wherein R is selected from the group consisting of hydrogen, lower alkyl; substituted lower alkyl; hydroxy lower alkyl; carboxy lower alkyl; carboxy, hydroxy lower alkyl; carboxy, halo lower alkyl; carboxy, dihydroxy lower alkyl; dicarboxy, hydroxy lower alkyl; carboxy lower alkenyl; dicarboxy lower alkenyl; phenyl; substituted phenyl and mixtures thereof, wherein substituted lower alkyl is substituted by one or more groups selected from the group consisting of consisting of halogen, hydroxyl, amino, thiol, nitro, and cyano.

3. The composition according to claim 1 wherein the organic acid is selected from the group consisting of citric, malic, succinic, lactic, glycolic, fumaric, tartaric, and formic acids and mixtures thereof.

4. The composition according to claim 1 wherein the (c) at least one polymer present in the composition is a vinyl pyrrolidone/acrylic acid copolymer.

5. The composition according to claim 1 wherein the (a) at least one organic acid is present in an amount of from about 0.01 to about 10% wt.

6. The composition according to claim 1 wherein the (c) at least one polymer is present in an amount of from about 0.01 to about 10% wt.

7. The composition according to claim 1 wherein the (b) at least one anionic surfactant is present.

8. The composition according to claim 7 wherein the (b) anionic surfactant is selected from the group consisting of alcohol sulfates and sulfonates, alkyl sulfates, alkylaryl sulfates, alkyl sulfonates, and alkylaryl sulfonates.

9. The composition according to claim 7 wherein the (b) anionic surfactant is present in an amount of from about 0.01 to about 10% wt.

10. The composition according to claim 1 wherein the ratio of (a):(b):(c) ranges from about 1:1:1 to about 6:2:1.

11. The composition according to claim 1 wherein the (b) at least one anionic surfactant is excluded from the composition.

12. A composition according to claim 1 comprising
(a) at least one organic acid selected from a compound having the formula:

wherein R is selected from the group consisting of hydrogen, lower alkyl; substituted lower alkyl; hydroxy lower alkyl; carboxy lower alkyl; carboxy, hydroxy lower alkyl; carboxy, halo lower alkyl; carboxy, dihydroxy lower alkyl; dicarboxy, hydroxy lower alkyl; carboxy lower alkenyl; dicarboxy lower alkenyl; phenyl; substituted phenyl and mixtures thereof, wherein substituted lower alkyl is substituted by one or more groups selected from the group consisting of consisting of halogen, hydroxyl, amino, thiol, nitro, and cyano;

(b) optionally, at least one anionic surfactant selected from alcohol sulfates and sulfonates, alcohol phosphates and phosphonates, alkyl ester sulfates, alkyl diphenyl ether sulfonates, ailcyl sulfates, alkyl ether sulfates, sulfate esters of an ailcyiphenoxy polyoxyethylene ethanol, alkyl monoglyceride sulfates, alkyl sulfonates, alkyl ether sulfates, alpha-olefm sulfonates, beta-alkoxy alkane sulfonates, alkyl ether sulfonates, ethoxylated alkyl sulfonates, alkylaryl sulfonates, alkylaryl sulfates, alkyl monoglyceride sulfonates, alkyl carboxylates, alkyl ether carboxylates, alkyl alkoxy carboxylates having 1 to 5 moles of ethylene oxide, alkylpolyglycolethersulfates containing up to 10 moles of ethylene oxide, sulfosuccinates, octoxynol or nonoxynol phosphates, taurates, fatty taurides, fatty acid amide polyoxyethylene sulfates, acyl glycerol sulfonates, fatty oleyl glycerol sulfates, alkyl phenol ethylene oxide ether sulfates, paraffin sulfonates, alkyl phosphates, isethionates, N-acyl taurates, alkyl succinamates and sulfosuccinates, alkylpolysaccharide sulfates, alkylpolyglucoside sulfates, alkyl polyethoxy carboxylates, and sarcosinates or mixtures thereof;

(c) at least one polymer capable of forming a complex with
(a) at least one of organic acid selected from the group a copolymer of vinyl pyrrolidone/acrylic acid and its esters; and a copolymer of vinyl pyrrolidone/methacrylic acid and its esters; and (d) from 60% to 90% by weight of at least one organic solvent;

(e) optionally, at least one propellant;

(f) water; and optionally, one or more further conventional constituents selected from the group consisting of: pH buffering agents, perfumes, perfume carriers, colorants, hydrotropes, viscosity modifying agents, further germicides, fungicides, anti-oxidants, and anti-corrosion agents.

13. The composition according to claim 1 wherein the residual antimicrobial benefit is against viruses.

14. The composition according to claim 1 wherein the composition is incorporated into a wipe.

15. The composition according to claim 10 wherein the ratio of (a):(b):(c) ranges from about 1:1:1 to about 4:2:1.

16. The composition according to claim 10 wherein the ratio of (a):(b):(c) ranges from about 1:1:1 to about 2:2:1.

17. The composition according to claim 1 wherein the organic solvent present is selected from the group consisting of: alcohols, glycols, glycol ethers, and ethers.

18. The composition according to claim 17 wherein the organic solvent present is selected from the group consisting of: methanol, ethanol, n-propanol, isopropanol, n-butanol and mixtures thereof.

19. The composition according to claim 1 wherein the composition exhibits residual antimicrobial performance after at least 1 rinse with water.

* * * * *